United States Patent [19]

Handrick et al.

[11] 4,243,590
[45] Jan. 6, 1981

[54] PROCESS FOR MAKING INDOLE

[75] Inventors: Kurt Handrick, Essen-Steele; Georg Kölling, Essen-Bredeney, both of Fed. Rep. of Germany

[73] Assignee: Bergwerksverband GmbH, Essen, Fed. Rep. of Germany

[21] Appl. No.: 41,516

[22] Filed: May 22, 1979

[30] Foreign Application Priority Data

May 26, 1978 [DE] Fed. Rep. of Germany ....... 2822907

[51] Int. Cl.$^3$ ............................................ C07D 209/08
[52] U.S. Cl. .................................. 260/319.1; 546/181
[58] Field of Search ...................... 260/319.1; 546/166, 546/181

[56] References Cited

U.S. PATENT DOCUMENTS 3,847,937  11/1974  Moggi et al. .......................... 546/181

OTHER PUBLICATIONS

Berichte, vol. 16 p. 738 (1883).
Hollins; Synthesis of Nitrogen Ring Compounds p. 145 (1924).
Elderfield; Heterocyclic Compounds, vol. 4 p. 283 (1952).
Thulheimer; Synthetic Methods; vol. 25:233 (1970), vol. 15:687 (1959).

Primary Examiner—Mary C. Lee
Attorney, Agent, or Firm—Michael J. Striker

[57] ABSTRACT

Process for making indole by subjecting 1,2,3,4-tetrahydroquinoline to a thermal decomposition at a reaction temperature of about 650° to 750° C. in a reactor filled with a substantially inert material and in the presence of steam. The starting product for this process is easily available and can easily be obtained by chemical reaction and the process itself has a high yield.

7 Claims, No Drawings

PROCESS FOR MAKING INDOLE

BACKGROUND OF THE INVENTION

The invention relates to a process for making indole.

Indole is a valuable material in the perfume industry and is used for the fixation of perfuming agents. It is also the starting material for the synthesis of the growth regulator indolyl-3-acetic acid. Indole is furthermore used for making the essential amino acid L-tryptophane (β-indolyl-alanine) which when added to animal feed in small amounts contributes to an increase of the meat production.

Indole is found in coal tar in an amount of only about 0.2%. Its separation from the materials present with it is difficult and results in losses of substance. The amount of indole which can be obtained from coal tar is insufficient to meet the increasing demands.

Indole can also be synthesized in different ways. Most of the prior art processes proceed from o-ethylaniline from which indole is obtained by dehydrocyclization in the gas phase. In this process o-ethylaniline is evaporated and subjected to a heat treatment at 400° to 700° C. in the presence of an inert carrier gas such as hydrogen, nitrogen or also steam, together with a dehydrogenation catalyst. Suitable catalysts are $Al_2O_3$ or $SiO_2$ onto which heavy metal oxides such as chromium, copper, molybdenum or vanadium oxides are deposited or the catalyst consists of precious metal carrier catalysts containing platinum or palladium. The conversion of the o-ethylaniline and the yield of indole depends greatly on the reaction conditions and the composition of the catalyst. The conversion usually is between 40 and 60%. The yield related to the converted o-ethylaniline is between 20 and 60% of the theoretical value. There have, however, already been obtained yields of above 80% of the theoretical amount. Byproducts of the prior art processes are aniline, o-toluidine and o-aminostyrene (West German accepted applications Nos. 22 24 556 and 24 01 017.)

The shortcomings of the processes proceeding from o-ethylaniline are caused by the fact that the making of the o-ehtylaniline by nitration of ethylbenzene and subsequent reduction of the nitro group involves substantial losses. Besides, the activity of the dehydrogenation catalysts decreases rapidly.

It has also become known to make indole from N-(β-hydroxyethyl)-aniline by esterifying the alcohol function of the N-(β-hydroxyethyl)-aniline in an organic environment with an inorganic or organic acid at a temperature between 0° and 200° C. in a first step, and then subjecting the thus formed ester in a second step at a temperature between 650° and 900° C. to a thermal tracking treatment (West German accepted application No. 23 28 284). This prior art process is also difficult and complex like the processes starting from o-ethylaniline because it involves several reaction and conversion steps.

The present invention therefore has the object to improve the availability of indole by a process which has a high yield and starts from a readily available starting product.

SUMMARY OF THE INVENTION

This object is accomplished by subjecting 1,2,3,4-tetrahydroquinoline to a thermal decomposition at a reaction temperature between 650° and 750° C. in a reactor filled with an inert material and in the presence of steam.

The conversion of the 1,2,3,4-tetrahydroquinoline to indole sets in at a temperature of about 600° C. upon separation of methane but proceeds more likely only at a temperature of 650° C. Therefore, temperatures of about 675° to 725° C. are necessary.

In order to suppress the formation of byproducts it is necessary to carry out the thermal decomposition in an atmosphere of steam. The amount of water in this case should be 3 to 12 mol per mol of 1,2,3,4-tetrahydroquinoline.

The reaction is carried out in that steam which is heated to between 250° and 300° C. is passed together with the 1,2,3,4-tetrahydroquinoline through a preheating zone of the reactor where the mixture is heated to about 500° C. Subsequently, the mixture is passed into the main reaction zone of the reactor which is filled with an inert or predominantly inert material. Particularly suitable packing materials are quartz wool or quartz glass shards.

The introduction of the mixture of steam and 1,2,3,4-tetrahydroquinoline is effected at such speed that the residence time of the starting and reaction products in the main reaction zone is only about 1 to 2 seconds. The waste gas that has not been condensed when the reaction mixture is cooled contains in addition to methane mainly hydrogen and small amounts of ethylene.

DETAILS OF THE INVENTION AND PREFERRED EMBODIMENT

The condensed portions of the reaction mixture are preferably taken up in an inert solvent, for instance benzene, toluene or methylene chloride and are thus separated from the aqueous phase. The organic phase then contains the indole, unreacted 1,2,3,4-tetrahydroquinoline, quinoline formed by the hydrogenation and as the main byproduct o-ethylbenzonitrile.

For further separation it is preferred to subject the organic phase to a fractionating distillation. As the first run there are separated the o-ethylbenzonitrile and very small amounts of formed benzonitrile and o-tolunitrile. As the next fraction there comes over the quinoline which has been formed by the dehydrogenation and unreacted 1,2,3,4-tetrahydroquinoline which latter two compounds are recycled into the starting product. The bottom product consists of the indole of high concentration.

This concentrated indole can be further processed in conventional manner to obtain indole of a high degree of purity. For instance the indole can be separated as a potassium salt of low solubility by treatment with potassium hydroxide. It is also possible to extract the indole from the bottom product of high concentration by means of a selective solvent such as water containing dimethyl sulfoxide or to subject the bottom product to an azeotropic distillation with diethylene glycol in order to separate the indole.

A preferred method is the following: The bottom product consisting of indole of high concentration is reacted with toluene. The solution is then subjected to brief stirring with cold dilute mineral acid, for instance 5% hydrochloric acid in order to remove the residual bases and is thereafter deacidified with a sodium hydroxide solution followed by evaporation of the toluene. The remaining crude indole is recrystallized from an aliphatic hydrocarbon, for instance n-heptane.

The yield of indole in this process is usually between 60 and 70% of the theoretical amount relative to the reacted 1,2,3,4-tetrahydroquinoline and the recovered quinoline.

The 1,2,3,4-tetrahydroquinoline which is used as the starting product can easily be made by the selective hydrogenation of quinoline. Preferred is a hydrogenation on a copper chromite catalyst at about 190° C. and a hydrogene pressure of about 100 bar. The hydrogenation in this case stops at the stage when the tetrahydro compound is formed. A purification of the product is not necessary in this method. It can be used for the thermal decomposition of indole in spite of small fractions of quinoline which may be present therein.

The following example further illustrates the invention.

EXAMPLE

The reaction was carried out in this case in a reactor of a length of 75 cm and a clear width of 4 cm. The reactor was filled with irregularly formed shards of quartz glass. The upper third of the reactor was adjusted to a temperature of 500° C. by means of an electrical heating device while the remaining part was set for a temperature of 685° C. From the top there were introduced 200 g (1.5 mol) of 1,2,3,4-tetrahydroquinoline (THC) and 270 g water (15 mol) in the form of steam per hour. The vapors discharged from the reactor were subjected to condensation. The condensed mixture was taken up in toluene and separated from the aqueous phase. The solvent was subsequently distilled off.

There were obtained per hour 181 g of a product that was determined by gas chromatography to consist of 31% indole, 18% quinoline, 37% THC and 10% o-ethylbenzonitrile. The balance consisted of other byproducts such as benzonitrile and o-tolunitrile. The indole yield was 64% of the theoretical amount relative to the converted THC and recovered quinoline.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. In a process for making indole of the type wherein 1,2,3,4-tetrahydroquinoline is reacted with steam in a reactor filled with an inert material, the improvement comprising introducing a mixture of 1,2,3,4-tetrahydroquinoline and steam, in a mol ratio between 1:3 and 1:12, at a reaction temperature of about 650° to 750° C., at such speed that the necessary residence time of the starting and reaction products in the main reaction zone is limited to about 1 to 2 seconds, and then isolating and recovering the indole from the reaction product, whereby a high yield of indole is obtained and formation of byproducts is suppressed.

2. The process of claim 1, wherein the reaction temperature is between 675° and 725° C.

3. The process of claim 1, wherein the reactor is filled with quartz wool or quartz glass shords.

4. The process of claim 1, further comprising the steps of preheating the steam to about 250° to 300° C. and passing it with the 1,2,3,4-tetrahydroquinoline through a preheat zone of the reactor in which the mixture is then preheated to about 500° C. prior to introduction into the main reaction zone.

5. The process of claim 1 wherein the condensed reaction mixture is taken up in an inert solvent and are thus separated from the aqueous solution, the indole being present in the organic phase together with unreacted 1,2,3,4-tetrahydroquinoline, quinoline formed by dehydrogenation and o-ethylbenzonitrile.

6. The process of claim 5 wherein the organic phase is then subjected to a fractional distillation wherein a high concentration indole is obtained in the bottom product after removal of two preceding fractions.

7. The process of claim 6 wherein the high concentration indole fraction is mixed with toluene whereupon the solution is briefly stirred with a cold dilute mineral acid to remove the residual bases followed by recrystallization of the crude indole from an aliphatic hydrocarbon.

* * * * *